(12) United States Patent
Smith et al.

(10) Patent No.: US 10,004,876 B2
(45) Date of Patent: Jun. 26, 2018

(54) TORQUE-TRANSMITTING, LOCKING INSTRUMENT HOLDER AND METHOD FOR OPERATING THE INSTRUMENT HOLDER

(71) Applicant: Syntheon, LLC, Miami, FL (US)

(72) Inventors: Kevin W. Smith, Coral Gables, FL (US); Matthew A. Palmer, Miami, FL (US); Derek Dee Deville, Coral Gables, FL (US); Korey Kline, Miami, FL (US); Carlos Rivera, Cooper City, FL (US)

(73) Assignee: Syntheon, LLC, Miami, FL (US)

( * ) Notice: Subject to any disclaimer, the term of this patent is extended or adjusted under 35 U.S.C. 154(b) by 0 days. days.

(21) Appl. No.: 15/617,373

(22) Filed: Jun. 8, 2017

(65) Prior Publication Data

US 2017/0266412 A1    Sep. 21, 2017

Related U.S. Application Data

(62) Division of application No. 12/121,132, filed on May 15, 2008, now Pat. No. 9,707,376.

(Continued)

(51) Int. Cl.
 *B25B 13/44* (2006.01)
 *B25B 25/00* (2006.01)
(Continued)

(52) U.S. Cl.
 CPC ......... *A61M 25/0105* (2013.01); *B25B 13/44* (2013.01); *B25B 13/5041* (2013.01);
(Continued)

(58) Field of Classification Search
 CPC ..... A61M 25/0105; A61M 2025/09116; A61B 1/31; B25B 25/00; B25B 13/5041;
(Continued)

(56) References Cited

U.S. PATENT DOCUMENTS 3,680,877 A * 8/1972 Happe ................ B23B 31/1253
   279/62
4,199,160 A * 4/1980 Bent ........................ A61C 1/14
   279/30

(Continued)

FOREIGN PATENT DOCUMENTS

JP            13087273       4/2001
KR         1020050031449    4/2005

OTHER PUBLICATIONS

International Search Report for PCT/US2008/064084 dated Dec. 9, 2008.

*Primary Examiner* — Bayan Salone
(74) *Attorney, Agent, or Firm* — Mayback & Hoffman, P.A.; Gregory L. Mayback; Rebecca A. Tie

(57) ABSTRACT

A torque-transmitting, locking instrument holder, includes a hollow body having a proximal end for receiving an instrument, a distal end for protrusion of the instrument, and a handle to be gripped by an operator. A device is provided for locking the handle to and unlocking the handle from the instrument at least partly disposed within the hollow body. A method for operating the instrument holder includes providing a hollow body having a proximal end for receiving an instrument, a distal end for protrusion of the instrument, and a handle to be gripped by an operator. The instrument is placed at least partly within the hollow body and the handle is locked to and unlocked from the instrument.

5 Claims, 11 Drawing Sheets

Related U.S. Application Data

(60) Provisional application No. 60/930,818, filed on May 18, 2007.

(51) Int. Cl.
  *A61B 1/31* (2006.01)
  *A61M 25/01* (2006.01)
  *B25B 13/50* (2006.01)
  *A61M 25/09* (2006.01)

(52) U.S. Cl.
  CPC ............... *B25B 25/00* (2013.01); *A61B 1/31* (2013.01); *A61M 2025/09116* (2013.01); *Y10T 279/17521* (2015.01); *Y10T 279/17564* (2015.01); *Y10T 279/17581* (2015.01); *Y10T 279/17589* (2015.01); *Y10T 279/17666* (2015.01); *Y10T 279/17743* (2015.01); *Y10T 279/17811* (2015.01)

(58) Field of Classification Search
  CPC ............. B25B 13/44; Y10T 279/17811; Y10T 279/17521; Y10T 279/17564; Y10T 279/17581; Y10T 279/17589; Y10T 279/17666; Y10T 279/17743
  USPC ............................ 279/50, 55–57, 66, 74, 82
  See application file for complete search history.

(56) References Cited

U.S. PATENT DOCUMENTS

| | | | | |
|---|---|---|---|---|
| 4,309,041 A * | 1/1982 | Peterson | ............... | B23B 31/202 279/46.7 |
| 4,366,733 A * | 1/1983 | Colvin | ................... | B25B 13/18 279/65 |
| 4,595,362 A * | 6/1986 | Ackermann | ............. | A61C 1/14 279/83 |
| 4,663,999 A * | 5/1987 | Colvin | ................... | B25B 13/18 279/65 |
| 4,858,938 A * | 8/1989 | Terwilliger | ........... | B23B 31/202 279/46.7 |
| 5,011,344 A * | 4/1991 | Johnson | ................ | B23B 31/107 279/74 |
| 5,067,376 A * | 11/1991 | Fosella | ................... | B25B 13/44 279/107 |
| 5,211,633 A * | 5/1993 | Stouder, Jr. | ........ | A61B 17/3462 604/167.03 |
| 5,213,015 A * | 5/1993 | Disston, Jr. | ............... | B25B 9/00 279/52 |
| 5,337,634 A * | 8/1994 | Carnesi | ............ | B23B 31/16162 279/65 |
| 5,833,405 A * | 11/1998 | Nielsen | ............... | B23B 31/1215 279/19.3 |
| 6,062,574 A * | 5/2000 | Yorde | ................... | B23B 31/202 279/46.3 |
| 6,073,522 A * | 6/2000 | Carnesi | .................. | B25B 13/44 279/114 |
| RE37,358 E * | 9/2001 | Del Rio | ............... | A61B 17/162 408/231 |
| 6,341,544 B1 * | 1/2002 | Falzone | .................. | B25B 13/44 81/128 |
| 6,347,914 B1 * | 2/2002 | Boyle | .................. | B23B 31/1074 408/226 |
| 6,382,636 B1 * | 5/2002 | Walker | ................ | B23B 31/1253 279/140 |
| 6,394,715 B1 * | 5/2002 | Boyle | .................. | B23B 31/1074 408/238 |
| 6,478,731 B2 * | 11/2002 | Speier | ............... | A61B 1/00135 600/121 |
| 6,786,685 B2 * | 9/2004 | Schaub | ............... | B23B 31/1071 279/75 |
| 6,818,005 B2 * | 11/2004 | Kupferschmid | ....... | A61B 17/29 279/30 |
| 6,821,120 B2 * | 11/2004 | Suzuki | ................... | A61C 1/144 433/129 |
| 7,040,630 B2 * | 5/2006 | Huggins | ............ | B23B 31/1071 279/62 |
| 7,080,964 B2 * | 7/2006 | Riley | .................. | B23B 31/1253 279/142 |
| 7,175,185 B2 * | 2/2007 | Chen | ..................... | B25B 15/001 279/75 |
| 7,219,581 B2 * | 5/2007 | Tulloch | ................... | B25B 13/48 279/51 |
| 7,448,870 B2 * | 11/2008 | Ma tre | .................... | A61C 1/144 433/114 |
| 7,645,138 B2 * | 1/2010 | Boinot | ................... | A61C 1/141 433/128 |
| 7,707,916 B2 * | 5/2010 | Pirseyedi | ................ | B25B 13/44 279/64 |
| D625,803 S * | 10/2010 | Studenec | ..................... | D24/133 |
| 7,811,228 B2 * | 10/2010 | Adams | ............... | A61B 1/00094 600/121 |
| 7,878,092 B1 * | 2/2011 | Eby | ........................ | B25B 7/02 81/112 |
| 7,947,000 B2 * | 5/2011 | Vargas | ............ | A61M 25/0021 600/587 |
| 7,959,162 B2 * | 6/2011 | Smith | ....................... | B25B 9/00 279/74 |
| 7,988,621 B2 * | 8/2011 | Smith | ................... | A61B 1/0055 600/144 |
| 8,066,456 B2 * | 11/2011 | Mohr | ..................... | B23B 31/02 279/55 |
| 8,075,001 B2 * | 12/2011 | Ghezzi | ................ | B23B 31/1269 279/57 |
| 9,707,376 B2 * | 7/2017 | Smith | ............... | A61M 25/0105 |
| 2005/0047878 A1 * | 3/2005 | Riley | .................. | B23B 31/1253 408/16 |
| 2006/0025652 A1 * | 2/2006 | Vargas | ............... | A61B 1/00154 600/114 |
| 2007/0043262 A1 * | 2/2007 | Levy | .................... | A61B 1/015 600/156 |
| 2007/0227311 A1 * | 10/2007 | Wang | ................... | B25B 13/06 81/125 |
| 2008/0091170 A1 * | 4/2008 | Vargas | .............. | A61M 25/0021 604/528 |
| 2008/0287739 A1 * | 11/2008 | Smith | ............... | A61M 25/0105 600/131 |

* cited by examiner

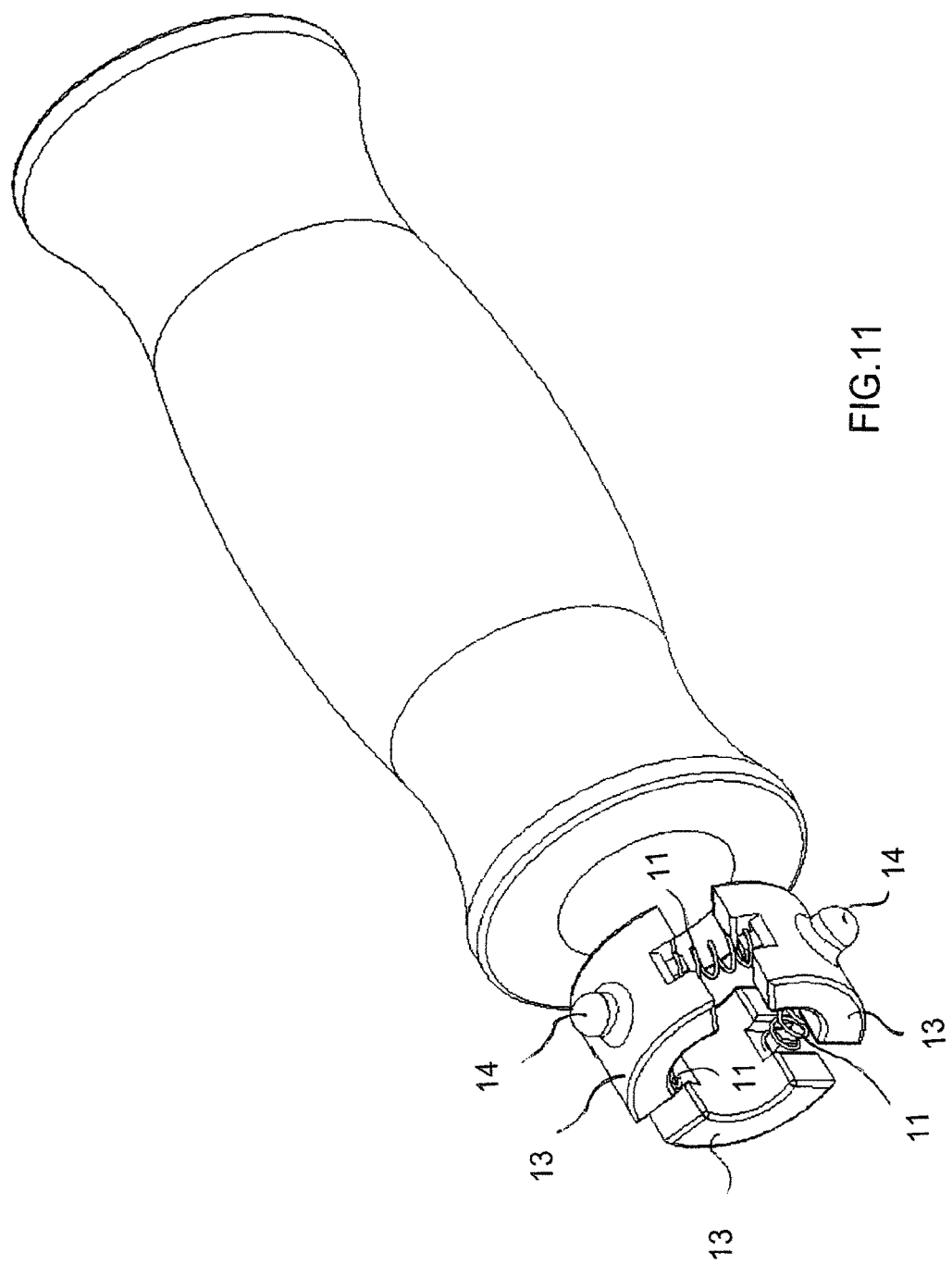

TORQUE-TRANSMITTING, LOCKING INSTRUMENT HOLDER AND METHOD FOR OPERATING THE INSTRUMENT HOLDER

CROSS-REFERENCE TO RELATED APPLICATION

The present application is a divisional of U.S. patent application Ser. No. 12/121,132, filed on May 15, 2008, which application claims priority, under 35 U.S.C. § 119, of U.S. Provisional Patent Application No. 60/930,818, filed on May 18, 2007, wherein the entire disclosures of these applications are all hereby incorporated herein by reference in their entireties.

STATEMENT REGARDING FEDERALLY SPONSORED RESEARCH OR DEVELOPMENT

N/A

FIELD OF THE INVENTION

The invention relates to a torque-transmitting, locking instrument holder. The invention also relates to a method for operating the instrument holder.

BACKGROUND OF THE INVENTION

Prior art devices and methods of this type have been complicated, making it difficult to torque and push an endoscope.

SUMMARY OF THE INVENTION

It is accordingly an object of the invention to provide a torque-transmitting, locking instrument holder and a method for operating the instrument holder, which overcome the hereinafore-mentioned disadvantages of the heretofore-known devices and methods of this general type and which permits simple yet reliable gripping of an instrument, in particular an endoscope or colonoscope, for circumferential and axial movement.

With the foregoing and other objects in view there is provided, in accordance with the invention, a torque-transmitting, locking instrument holder. The instrument holder comprises a hollow body having a proximal end for receiving an instrument, a distal end for protrusion of the instrument, and a handle to be gripped by an operator. A device is provided for locking the handle to and unlocking the handle from the instrument at least partly disposed within the hollow body.

With the objects of the invention in view, there is also provided a method for operating a torque-transmitting, locking instrument holder. The method comprises providing a hollow body having a proximal end for receiving an instrument, a distal end for protrusion of the instrument, and a handle to be gripped by an operator. The instrument is placed at least partly within the hollow body and the handle is locked to and unlocked from the instrument.

In accordance with another feature of the invention, the locking and unlocking device includes an actuator to be activated by the operator for locking the handle to and unlocking the handle from the instrument. The actuator may be a bobbin to be slid by an operator.

In accordance with a further feature of the invention, the locking and unlocking device includes a clamping plate disposed within the actuator. The clamping plate is moved radially inwardly against the instrument and radially outwardly away from the instrument by activating the actuator. The clamping plate may include a plurality of partial-plates, at least one spring biasing the partial-plates radially outwardly and detents integral with the partial-plates. The detents are disposed in recesses in the actuator in an unlocked condition and slide out of the recesses and push the partial-plates towards the instrument against a force of the at least one spring into a locked condition.

In accordance with a further feature of the invention, there is provided a body tube disposed partially within the handle and having a coupling end disposed within the actuator. The coupling end has slots formed therein within which the detents slide between the locked and unlocked conditions.

In accordance with a concomitant feature of the invention, stops limit motion of the actuator into the locked and unlocked conditions.

Other features which are considered as characteristic for the invention are set forth in the appended claims.

Although the invention is illustrated and described herein as embodied in a torque-transmitting, locking instrument holder and a method for operating the instrument holder, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 11 is a perspective view of the instrument holder with a coupler removed.

DETAILED DESCRIPTION OF THE INVENTION

Figure 1:
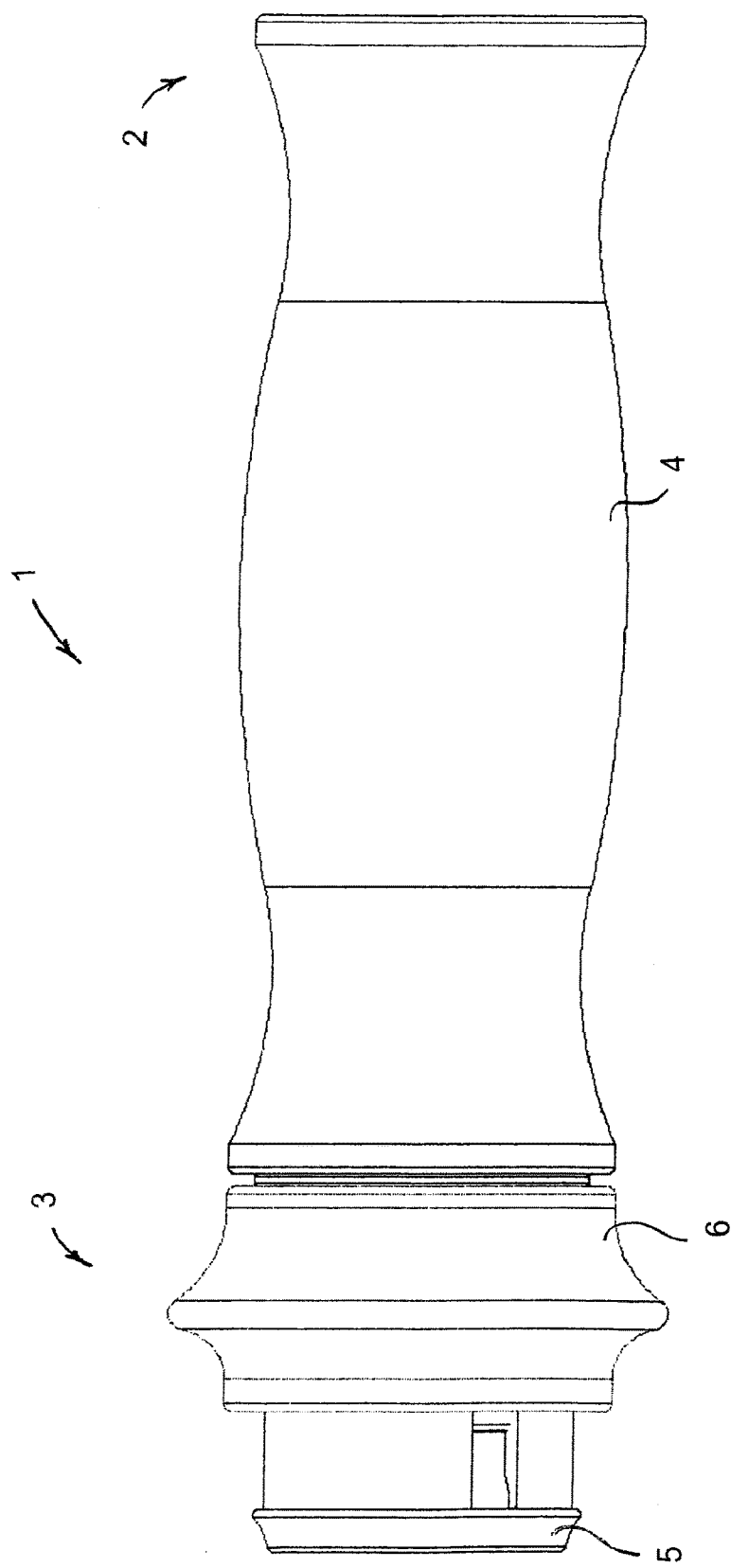
FIG. 1 is a diagrammatic, side-elevational view of a torque-transmitting, locking instrument holder according to the invention, approaching an unlocked condition.
Figure 2:
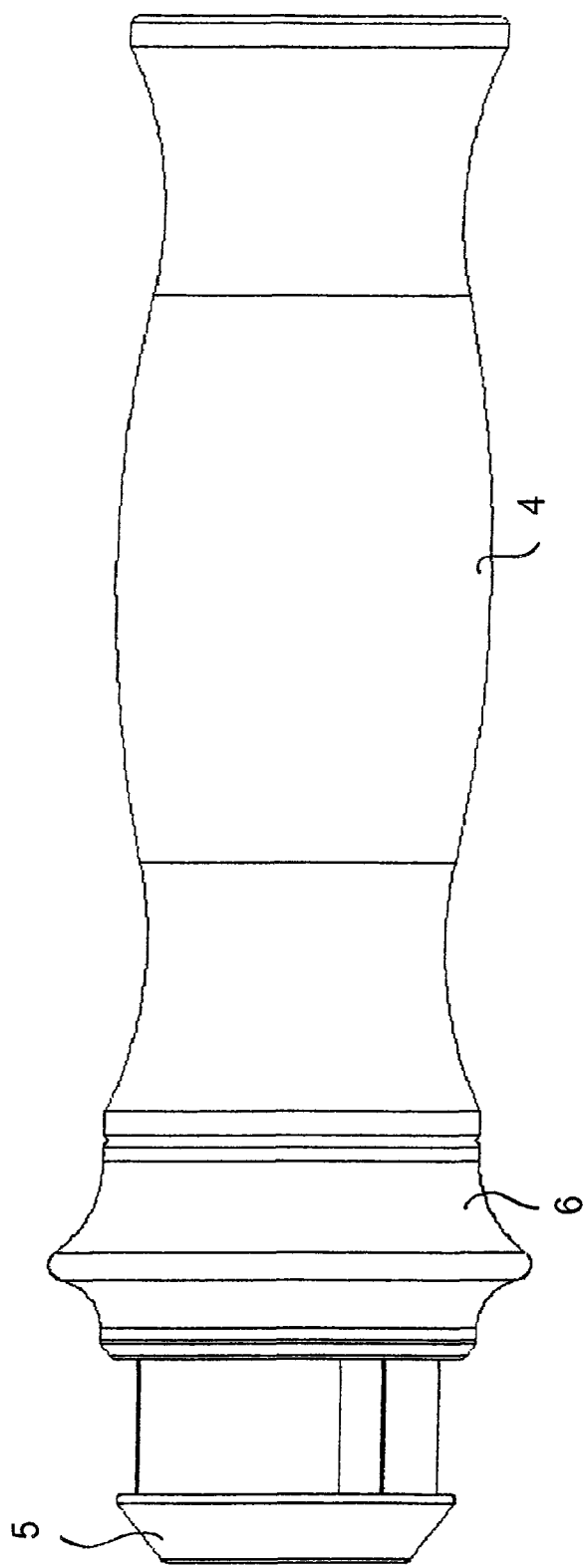
FIG. 2 is a view similar to FIG. 1 of the instrument holder in the unlocked condition.
Figure 3:
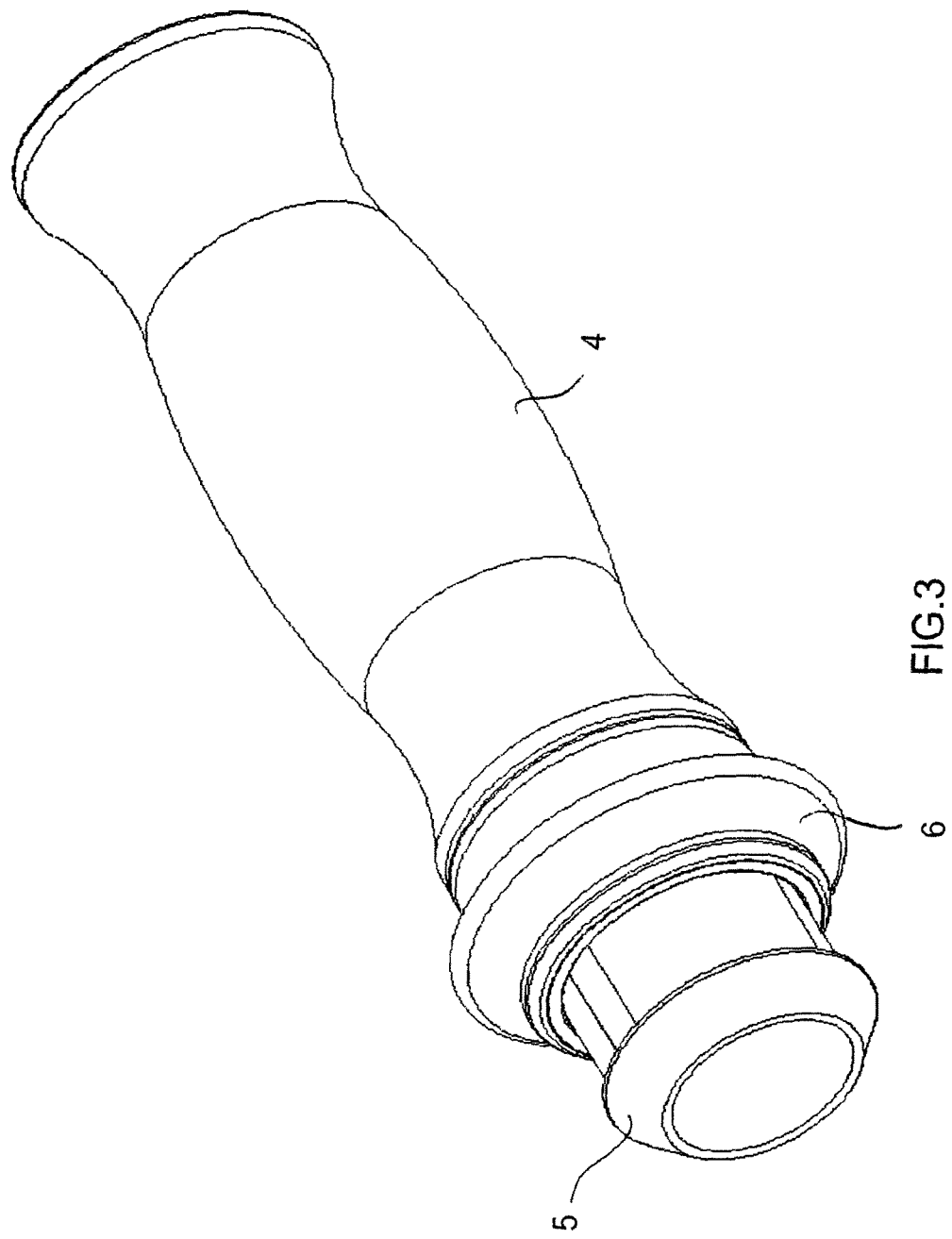
FIG. 3 is a perspective view of the instrument holder in the unlocked condition.
Figure 4:
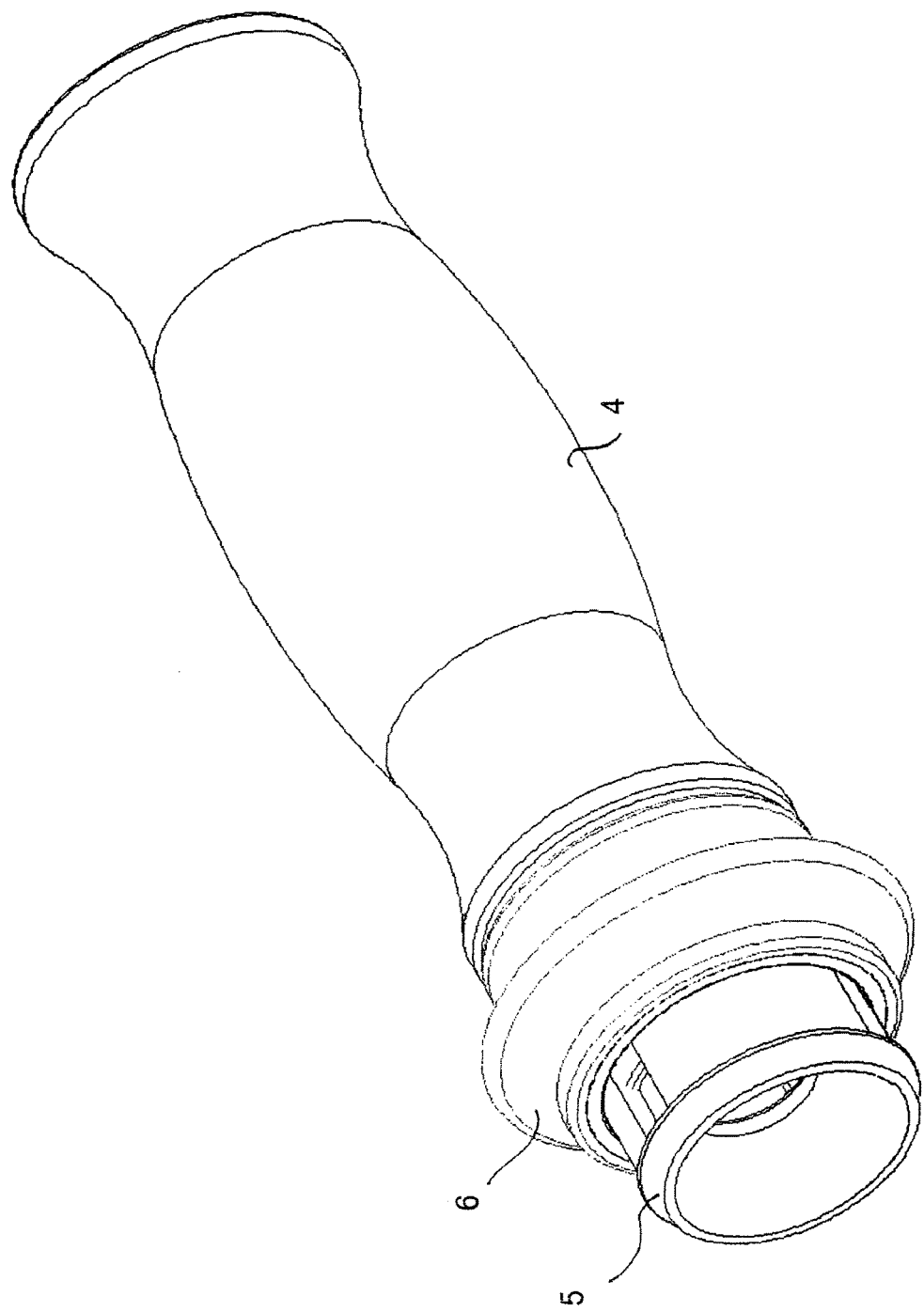
FIG. 4 is another perspective view of the instrument holder in the unlocked condition.

Referring now to the figures of the drawings in detail and first, particularly, to FIG. 1 thereof, there is seen a torque-transmitting, locking instrument holder 1 according to the invention, having a proximal end 2 and a distal end 3. The instrument holder 1 has a handle or grip 4 at the proximal end 2 and a rear bushing 5 at the distal end 3. It may also be seen from FIG. 1 that a bobbin 6 has been slid almost as far as possible toward the proximal end 2, into an unlocking position, which will be explained in greater detail below. When comparing FIGS. 1 and 2, it may be seen that the bobbin 6 has been fully slid toward the proximal end 2 in FIG. 2. FIGS. 3 and 4 similarly show perspective views of the instrument holder 1.

Figure 5:
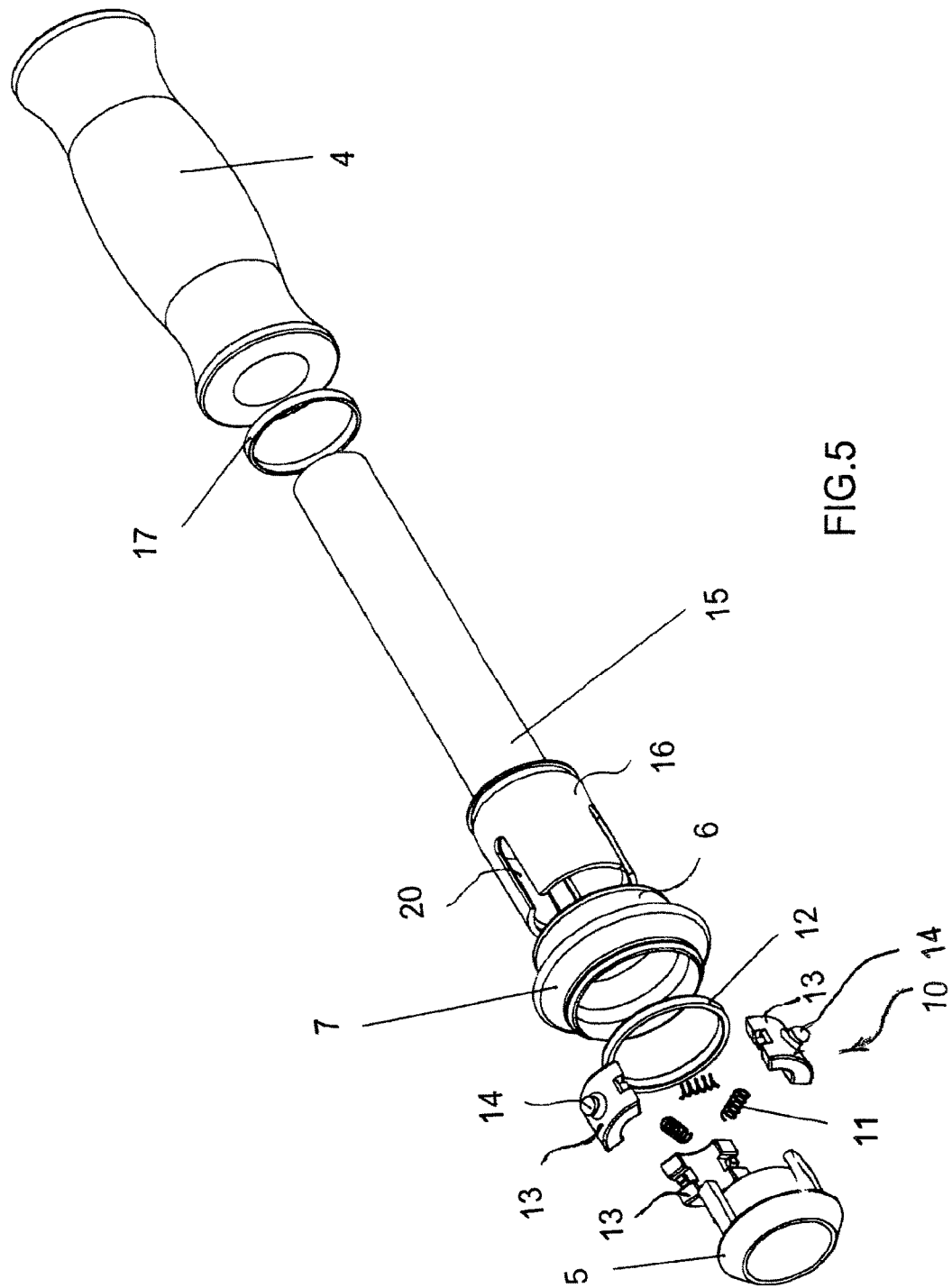
FIG. 5 is an exploded, perspective view of the instrument holder.

The instrument holder 1 is shown in greater detail in an exploded view in FIG. 5. Looking from the distal end 3 toward the proximal end 2, there is seen the rear bushing 5, a clamping plate 10 having clamping springs 11, a bobbin ring 12, the bobbin 6 having a bobbin rib 7, a body tube 15 having a coupling end 16, a marker band 17 and the handle or grip 4. The clamping plate 10 includes three partial-plates or partial-shells 13 each having a detent 14.

Figure 6:
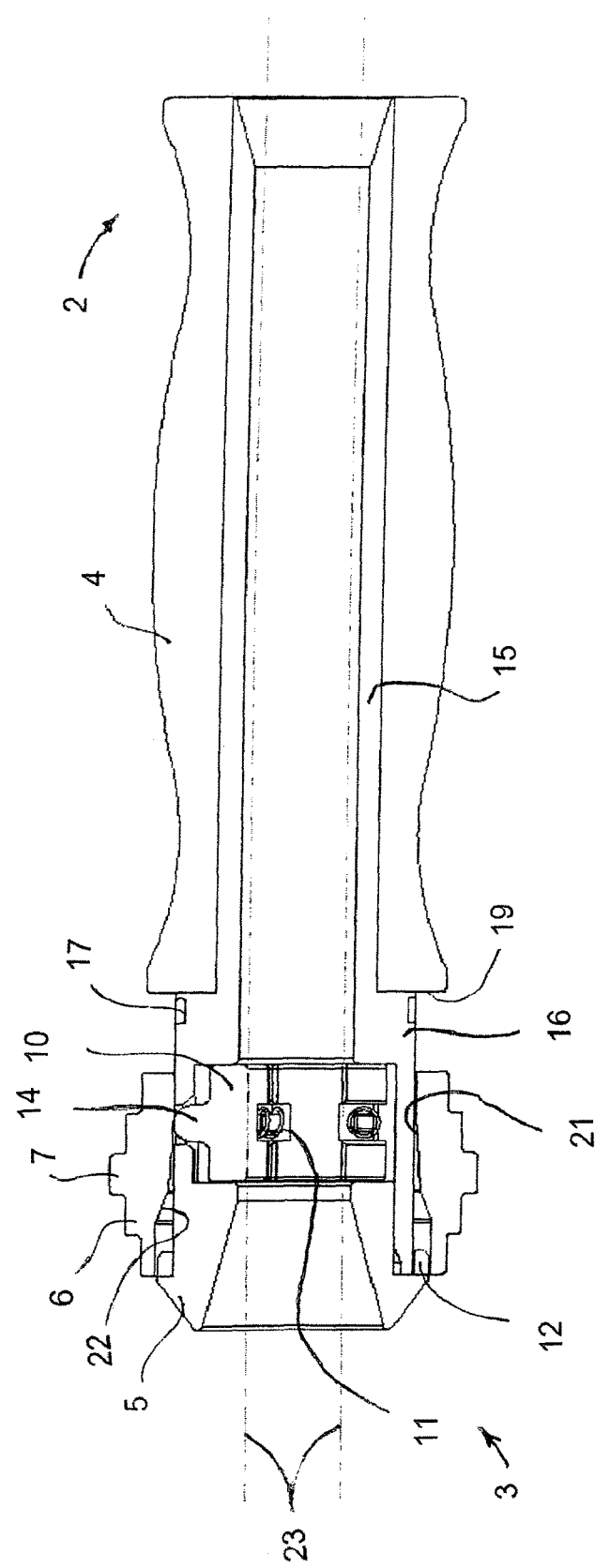
FIG. 6 is a longitudinal-sectional view of the instrument holder in the locked condition.
Figure 7:
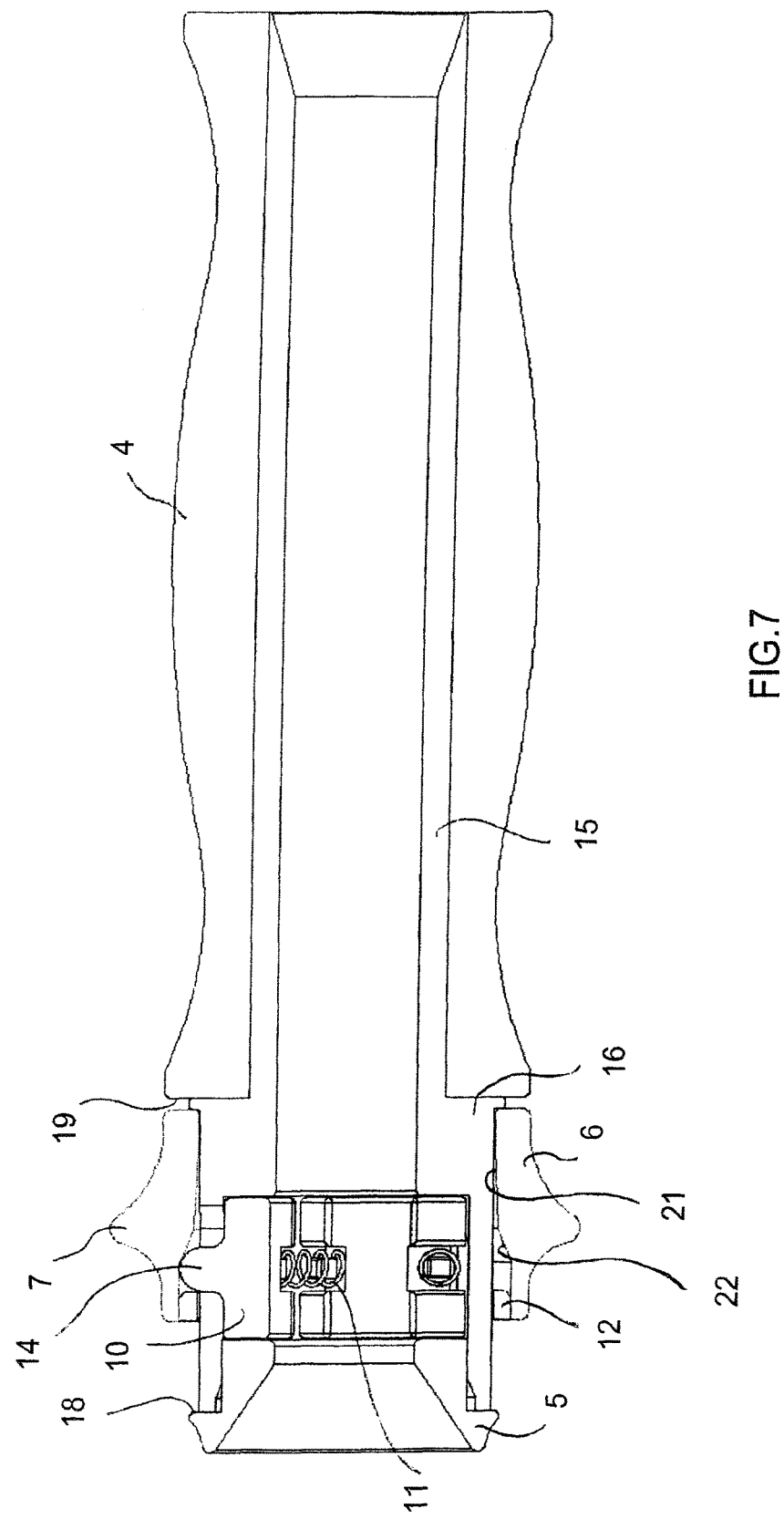
FIG. 7 is a view similar to FIG. 6 of the instrument holder in the condition shown in FIG. 1.
Figure 8:
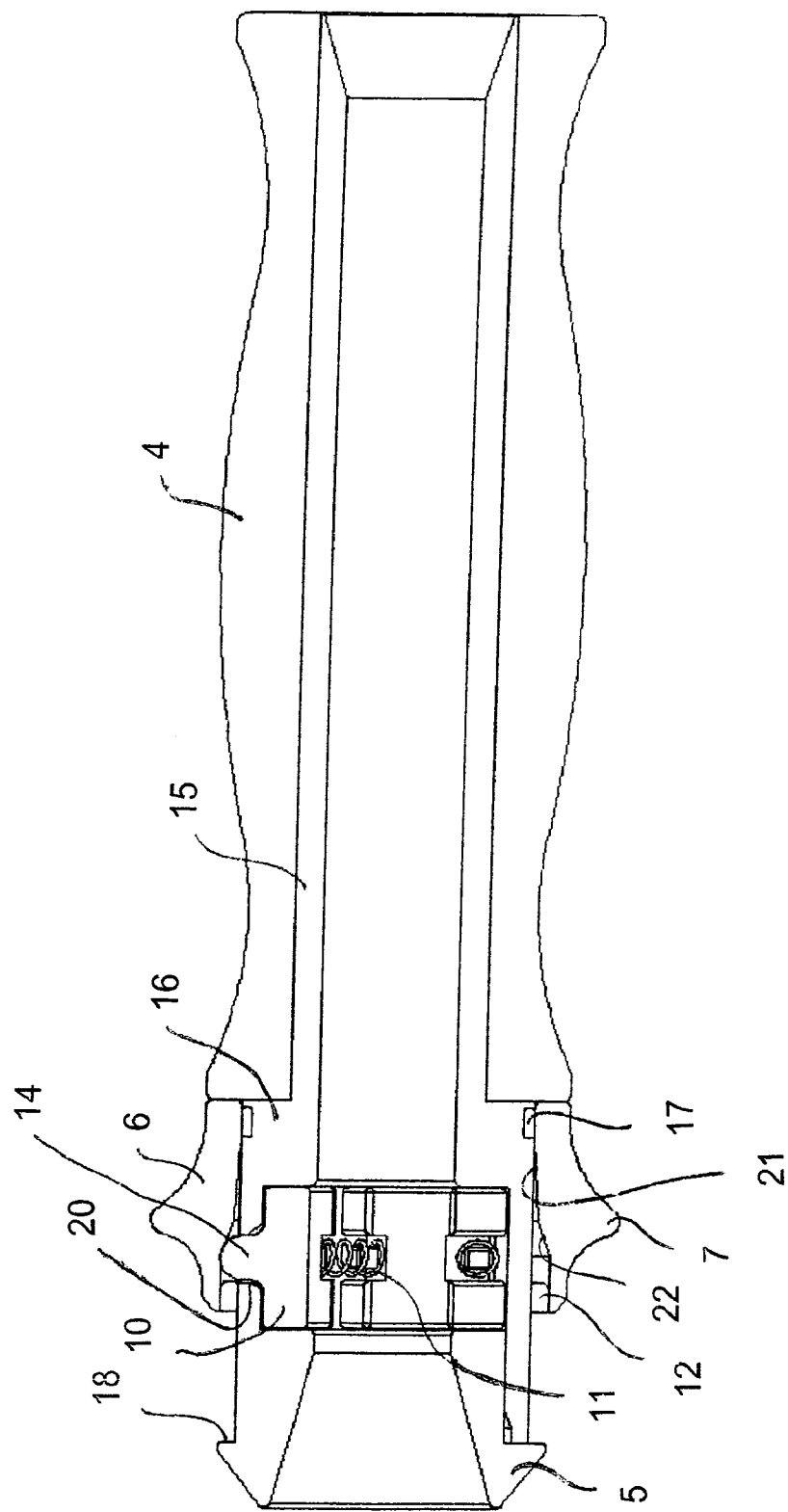
FIG. 8 is a view similar to FIGS. 6 and 7 of the instrument holder in the condition shown in FIG. 2.

FIGS. 6, 7 and 8 are longitudinal-sectional views in which the bobbin 6 is disposed in different positions. In FIG. 6, the bobbin 6 is slid distally against a stop 18, in FIG. 7, the bobbin 6 is slid proximally toward a stop 19 and in FIG. 8, the bobbin 6 is slid close to the stop 19. FIGS. 6, 7 and 8 also show that an inner peripheral surface 21 of the bobbin 6 has a recess 22.

Figure 9:
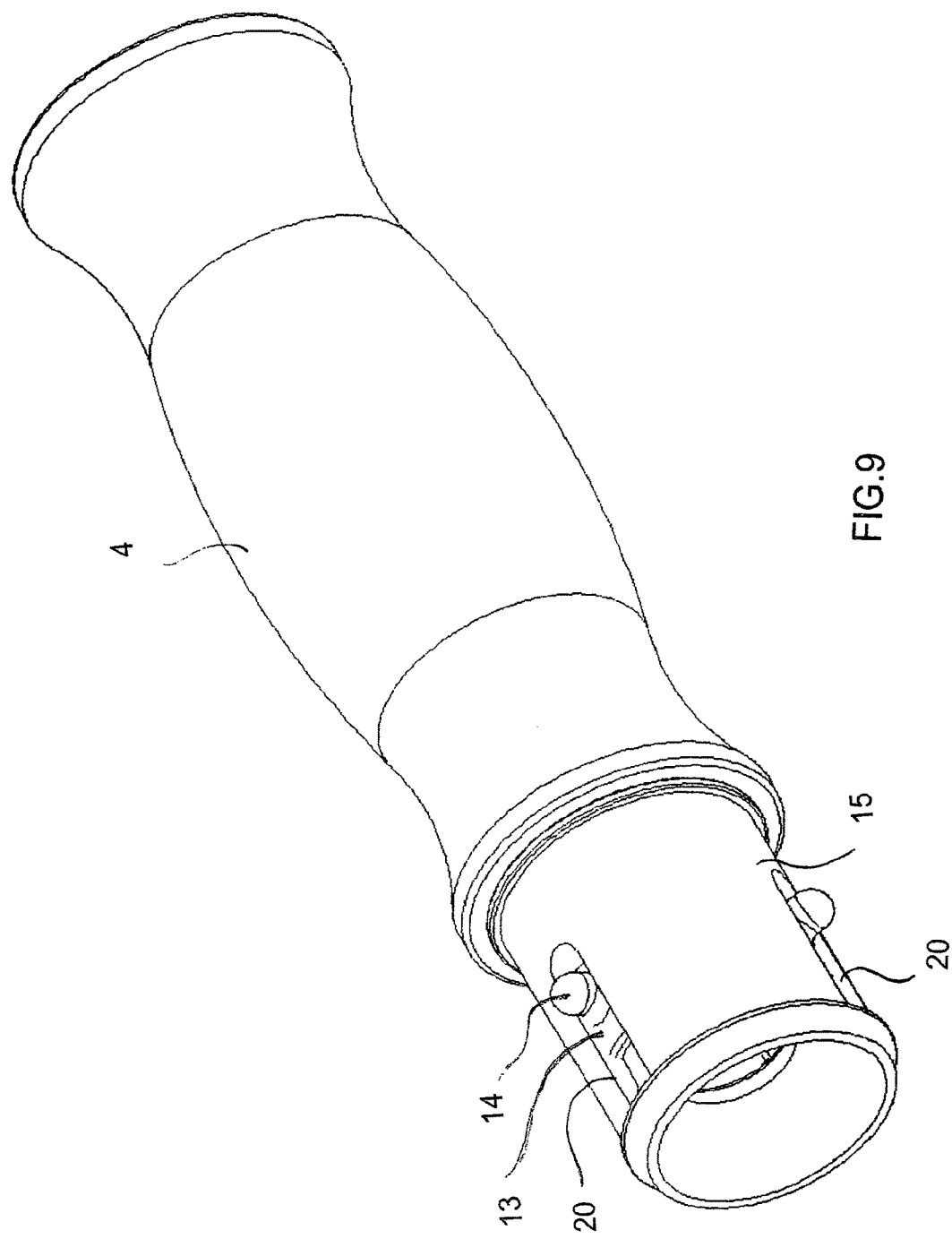
FIG. 9 is a perspective view of the instrument holder with a bobbin removed.
Figure 10:
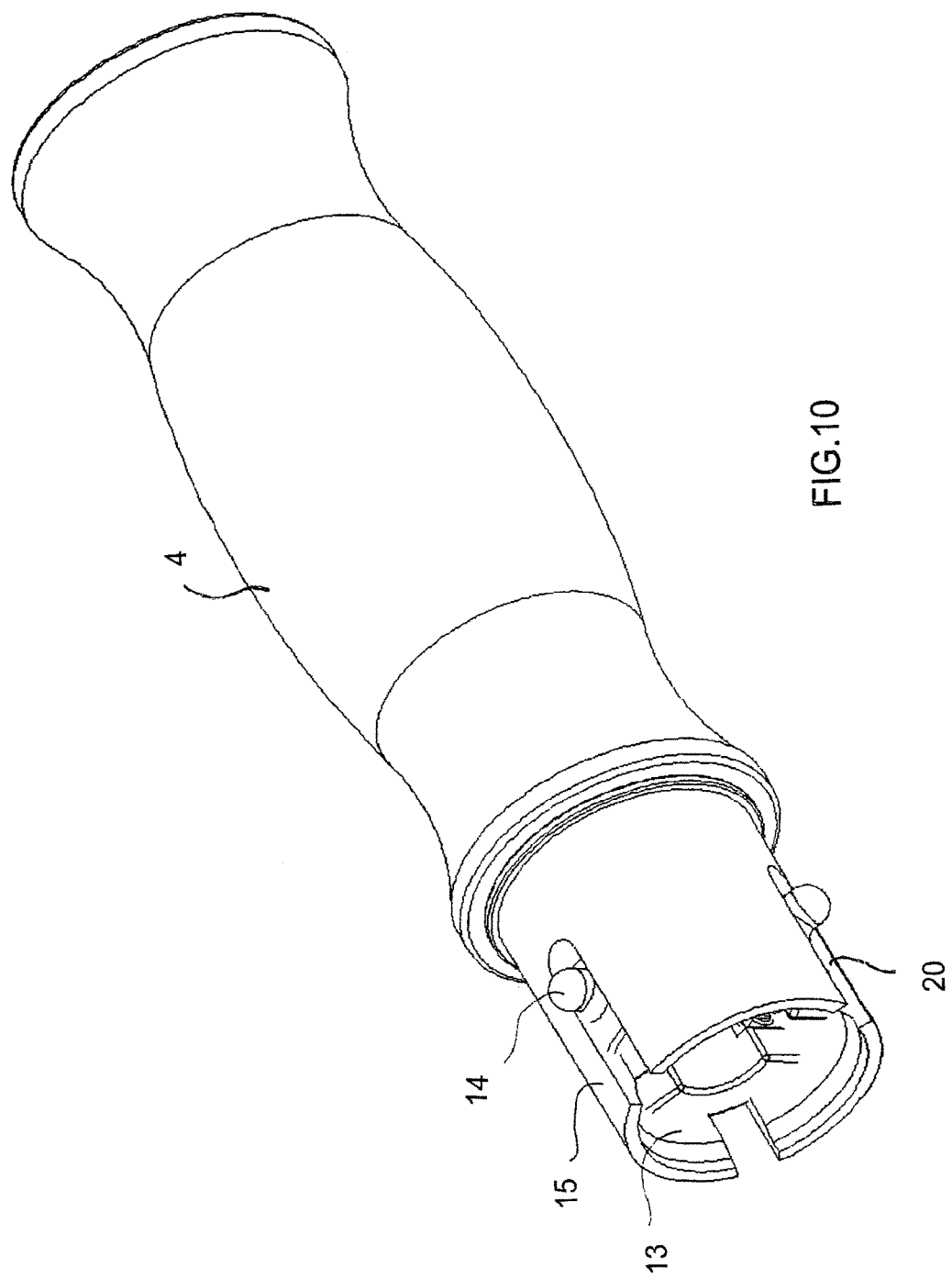
FIG. 10 is a perspective view of the instrument holder with a rear bushing removed.

In FIGS. 9 and 10, the bobbin 6 has been omitted to show the coupling end 16 of the body tube 15 protruding from the handle or grip 4. It may also be seen that the detents 14 each protrude through a respective slot 20 in the coupling end 16.

In FIG. 11, the coupling end 16 has also been omitted, so as to show the springs 11 mounted between the partial-plates 13 of the clamping plate 10.

The operation of the instrument holder 1 will now be explained with the aid of the drawings. An instrument 23, such as a colonoscope or an endoscope, which is diagrammatically shown in FIG. 6, is initially slid into a hollow body formed by the rear bushing 5, the bobbin 6, the body tube 15 and the handle or grip 4. The instrument 23 is inserted into the hollow body with the instrument holder 1 in an unlocked condition shown in FIG. 8. In the unlocked condition, the bobbin 6 is located proximally against the stop 19 and the springs 11 bias the partial-plates 13 radially outwardly. The detents 14 therefore protrude through the slots 20 against the recess 22 of the inner peripheral surface 21 of the bobbin 6.

When it is desired to lock the instrument holder 1 against the instrument 23, an operator pushes the bobbin rib 7 of the bobbin 6 distally from the position shown in FIG. 8, past the position shown in FIG. 7 and toward the position shown in FIG. 6, so that the instrument holder 1 enters the locked condition but may not reach the stop 18. As the bobbin 6 moves distally, the detents 14 slide along from the recess 22 to the inner peripheral surface 21 of the bobbin 6. This in turn pushes the partial-plates 13 radially inwardly against the force of the springs 11 and against the instrument 23, as shown in FIG. 6. The instrument 23 can therefore be manipulated by gripping and moving the handle 4. The instrument 23 is then released by sliding the bobbin 6 proximally once again.

What is claimed is:

1. A method for operating a torque-transmitting, locking instrument holder, the method comprising the following steps:
   providing a hollow body having a proximal end for receiving an instrument, a distal end for protrusion of the instrument, and a handle to be gripped by an operator;
   placing the instrument at least partly within the hollow body; and
   locking the handle to and unlocking the handle from the instrument, which comprises the operator activating an actuator that is at least partly disposed within the hollow body, wherein activating the actuator moves a clamping plate disposed within the actuator radially inward against the instrument and radially outward away from the instrument.

2. The method according to claim 1, wherein the actuator is a bobbin to be slid by an operator.

3. The method according to claim 1, wherein the clamping plate includes a plurality of partial-plates, at least one spring biasing the partial-plates radially outwardly and detents integral with the partial-plates, and the locking and unlocking step includes placing the detents in recesses in the actuator in an unlocked condition and sliding the detents out of the recesses to push the partial-plates towards the instrument against a force of the at least one spring into a locked condition.

4. The method according to claim 3, which further comprises providing a body tube disposed partially within the handle and having a coupling end disposed within the actuator, and sliding the detents in slots formed in the coupling end, when moving the actuator between the locked and unlocked conditions.

5. The method according to claim 3, which further comprises limiting motion of the actuator into the locked and unlocked conditions with stops.

* * * * *